(12) United States Patent
Chu

(10) Patent No.: US 7,441,296 B2
(45) Date of Patent: Oct. 28, 2008

(54) MOTORIZED INTERDENTAL TOOTHBRUSH

(76) Inventor: Henry C. Chu, 133N. Lemon St., Orange, CA (US) 92866

( * ) Notice: Subject to any disclaimer, the term of this patent is extended or adjusted under 35 U.S.C. 154(b) by 0 days.

(21) Appl. No.: 11/715,060

(22) Filed: Mar. 6, 2007

(65) Prior Publication Data

US 2008/0216265 A1 Sep. 11, 2008

(51) Int. Cl.
*A46B 13/02* (2006.01)
(52) U.S. Cl. .......................................................... 15/23
(58) Field of Classification Search ...................... 15/23, 15/22.1
See application file for complete search history.

(56) References Cited

U.S. PATENT DOCUMENTS

| | | | |
|---|---|---|---|
| 4,395,943 A | 8/1983 | Brandli | |
| 4,691,404 A | 9/1987 | Tarrson et al. | |
| 5,309,596 A | 5/1994 | Simms | |
| 5,488,751 A | 2/1996 | Gekhter et al. | |
| 5,613,258 A | 3/1997 | Hilfinger et al. | |
| 5,699,578 A * | 12/1997 | Dumler et al. | ............. 15/167.1 |
| 5,862,559 A * | 1/1999 | Hunter | ......................... 15/28 |

* cited by examiner

*Primary Examiner*—Randall Chin
(74) *Attorney, Agent, or Firm*—Charles E. Baxley

(57) ABSTRACT

A motorized interdental toothbrush includes one or more wires having fixed filaments, and a gage disposed on one end portion of the wires and having an outer diameter equal to or smaller than that of the filaments for limiting the wires and the filaments to engage into the selected interdental spaces between the teeth of the user and for preventing the filaments from being inserted and engaged into the interdental spaces having a relatively smaller width and for preventing the user's gum from being injured by the greater filaments, and a rotating device may be coupled to rotate and drive the brush device to clean the interdental space.

10 Claims, 3 Drawing Sheets

MOTORIZED INTERDENTAL TOOTHBRUSH

BACKGROUND OF THE INVENTION

1. Field of the Invention

The present invention relates to an interdental toothbrush, and more particularly to a motorized interdental toothbrush including a motor driving device coupled to the interdental toothbrush for rotating or driving the interdental toothbrush and for allowing the interdental spaces to be suitably cleaned by the motorized interdental toothbrushes.

2. Description of the Prior Art

Typical interdental toothbrushes comprise one or more twisted wires having fixed filaments between turns of the wire or wires for inserting or engaging into the interdental spaces between the teeth and particularly designed for cleaning the hard-to-reach interdental spaces between the teeth of the users.

For example, U.S. Pat. No. 4,395,943 to Brandli discloses one of the typical interproximal toothbrushes also comprise one or more twisted wires having fixed filaments between turns of the wire or wires for inserting or engaging into the interdental spaces between the teeth. Normally, two or more brushes or refills having different shapes or sizes or diameters may be provided in one package of the typical interproximal toothbrushes.

However, when the interdental toothbrushes of greater sizes or diameters are forced to be inserted or engaged into the interdental spaces having relatively smaller sizes or widths, the gum of the user may be hurt or injured by the interdental toothbrushes. In addition, the twisted wires may also have a good chance to hurt or injure the gum of the user when the twisted wires of the interdental toothbrushes are not precisely engaged into the interdental spaces between the teeth.

U.S. Pat. No. 4,691,404 to Tarrson et al., U.S. Pat. No. 5,309,596 to Simms, and U.S. Pat. No. 5,488,751 to Gekhter et al. disclose three further typical interproximal toothbrushes each comprise a handle, and one or more twisted wires secured to the handle and having fixed filaments between turns of the wire or wires for allowing the interproximal toothbrushes to be suitably inserted or engaged into the interdental spaces between the teeth with the handles.

However, the interdental toothbrushes may not be rotated or driven by any motor driving device and have to be operated manually. In addition, when the fixed filaments of greater sizes or diameters are inadvertently forced or inserted or engaged into the interdental spaces having relatively smaller sizes or widths, the gum of the user may be seriously hurt or injured by the interdental toothbrushes.

U.S. Pat. No. 5,613,258 to Hilfinger et al. discloses a still further typical interproximal toothbrush comprising a handle, one or more twisted wires secured to the handle and having fixed filaments between turns of the wire or wires, and a motor drive mechanism for driving the bristle array in oscillating rotary motion about the axis of the stem, and for allowing the interproximal toothbrushes to be suitably inserted or engaged into the interdental spaces between the teeth with the handles.

However, when the fixed filaments of greater sizes or diameters are inadvertently forced or inserted or engaged into the interdental spaces having relatively smaller sizes or widths and when the greater filaments are rotated relative to the gum and the teeth of the user, the gum of the user may be seriously hurt or injured by the interdental toothbrushes.

The present invention has arisen to mitigate and/or obviate the afore-described disadvantages of the conventional interdental toothbrushes.

SUMMARY OF THE INVENTION

The primary objective of the present invention is to provide a motorized interdental toothbrush including a motor driving means or device coupled to the interdental toothbrush for rotating or driving the interdental toothbrush and for allowing the interdental spaces to be suitably cleaned by the motorized interdental toothbrushes.

The other objective of the present invention is to provide a motorized interdental toothbrush including a gage for guiding the interdental toothbrush to be inserted or engaged into the predetermined or suitable interdental spaces between the teeth and for preventing the interdental toothbrushes of greater sizes or diameters from being inserted or engaged into the interdental spaces having relatively smaller sizes or widths.

In accordance with one aspect of the invention, there is provided a motorized interdental toothbrush comprising a brush device including at least one wire, and a number of filaments disposed on the wire for inserting and engaging into an interdental space between teeth of a user, and a gage disposed on a free end portion of the wire and having an outer diameter corresponding to that of the filaments for limiting the wire and the filaments to engage into a predetermined interdental space between the teeth of the user and for preventing the filaments from being inserted and engaged into an interdental space having a relatively smaller width and for preventing the user's gum from being hurt or injured by the filaments, and a rotating device for rotating the brush device to clean the interdental space between the teeth of the user.

The rotating device includes a handle, and a motor disposed in the handle and coupled to the wire of the brush device for rotating and driving the wire and the filaments of the brush device to clean the interdental space.

The motor includes a spindle coupled to the wire of the brush device. The rotating device includes one or more batteries disposed in the handle and coupled to the motor for energizing the motor to rotate the brush device.

The wire includes a wire segment provided thereon and located between the gage and the filaments. The gage includes an outer diameter equal to or smaller than that of the filaments.

The gage is made of soft materials for preventing the user's gum from being hurt and injured by the wire. The gage includes a rounded structure or a spherical structure for further preventing the user's gum from being hurt or injured by the filaments.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
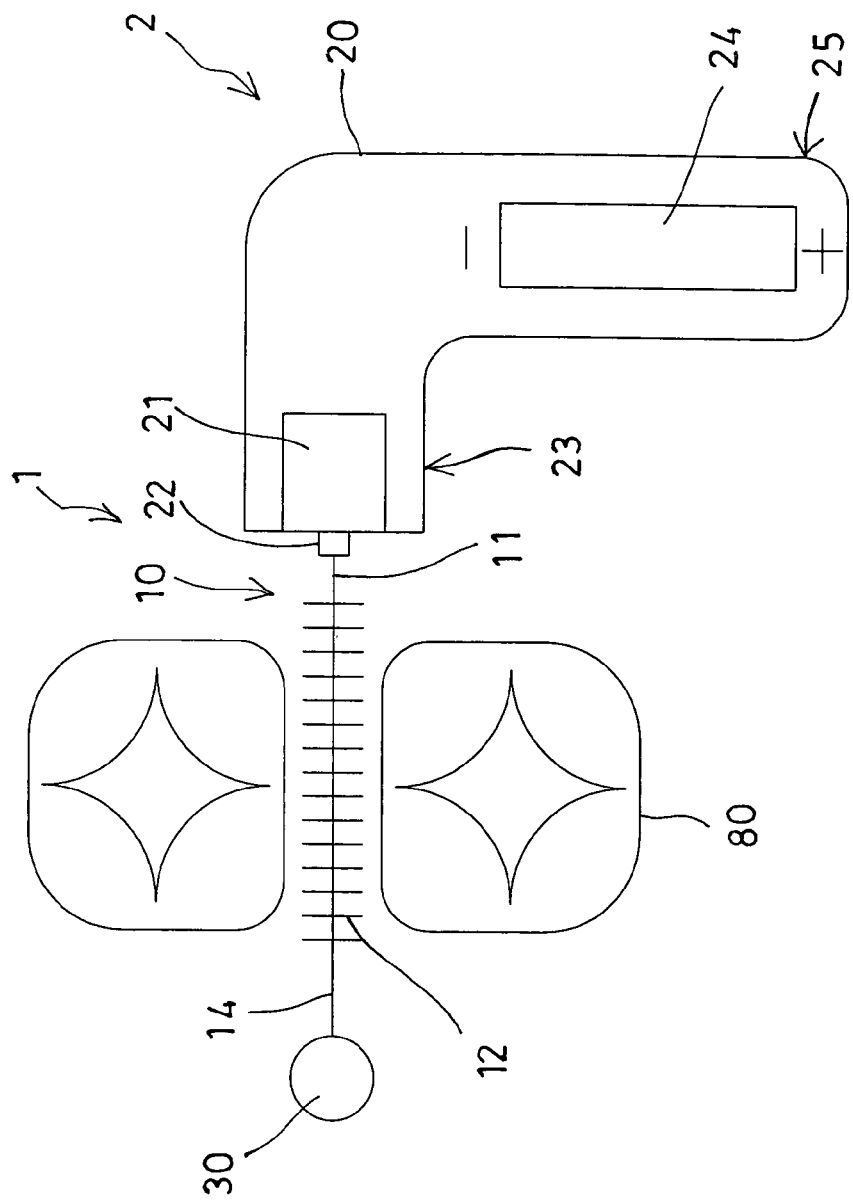
FIG. 1 is a plan schematic view illustrating the operation of a motorized interdental toothbrush in accordance with the present invention for being inserted or engaged into the interdental spaces between the teeth of the user.
Figure 2:
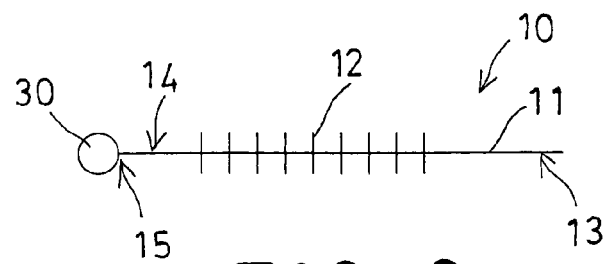
FIG. 2 is a partial plan schematic view illustrating one of the interdental toothbrushes.
Figure 3:
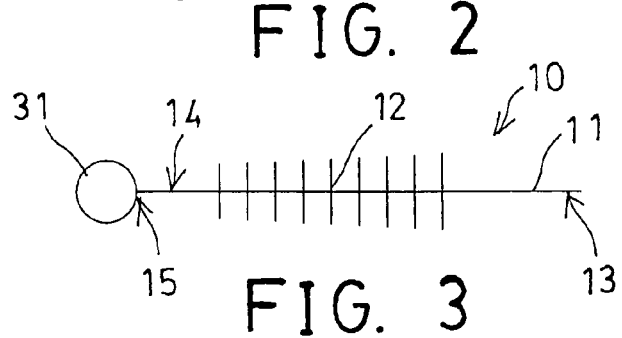
FIG. 3 is a partial plan schematic view similar to FIG. 2, illustrating the other interdental toothbrush.

Referring to the drawings, and initially to FIGS. 1 and 2, a motorized interdental toothbrush 1 in accordance with the present invention comprises a brush device 10 including one or more twisted wires 11 having fixed filaments 12 disposed or attached between turns of the wire or wires 11 for inserting or engaging into the interdental spaces a or b or c (FIG. 7) between the teeth 80 of the user and particularly designed for cleaning the hard-to-reach interdental spaces a or b or c between the teeth of the users. The filaments 12 may also be formed into or selected from various kinds of different shapes or contours or sizes or diameters, such as the ultra fine cylindrical shapes (FIG. 2), the ultra fine tapered shapes (FIG. 3), the cylindrical shapes (FIG. 4), the tapered shapes (FIG. 5), the large cylindrical shapes (FIG. 6), or the like.

Figure 5:
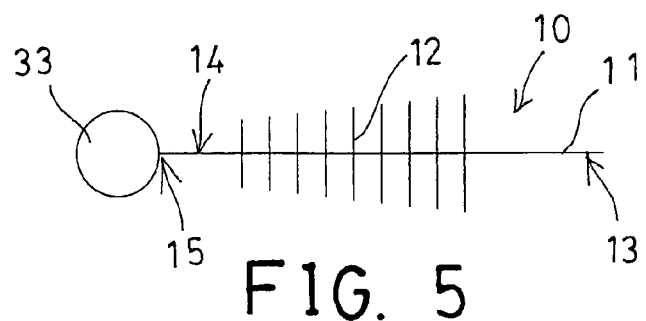
FIG. 5 is a partial plan schematic view similar to FIGS. 2-4, illustrating the still further interdental toothbrush.
Figure 6:
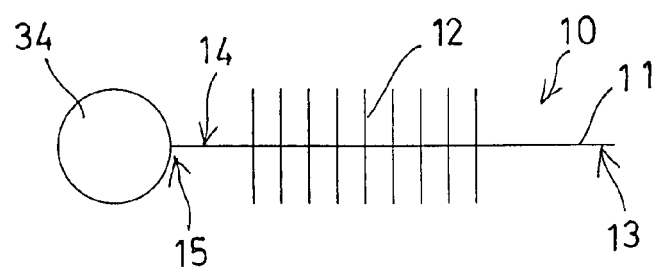
FIG. 6 is a partial plan schematic view similar to FIGS. 2-5, illustrating the still further interdental toothbrush.

For example, the filaments 12 of the ultra fine cylindrical shapes (FIG. 2) may include a size or diameter smaller than that of the cylindrical shapes (FIG. 4) which may include a size or diameter smaller than that of the large cylindrical shapes (FIG. 6). Similarly, the filaments 12 of the ultra fine tapered shapes (FIG. 3) may include a size or diameter smaller than that of the tapered shapes (FIG. 5). Normally, in one refill package of the interproximal toothbrushes 1, either or some or all of the refills or brush devices 10 of that shown in FIGS. 2-6 may include the filaments 12 of different shapes or sizes or diameters that may be selectively provided and contained in the package. The wire or wires 11 and the filaments 12 are typical or conventional and will not be described in further details.

The first or rear end portion 13 of the wires 11 may be attached to a power or motor driving or rotating means or device 2 which includes a handle 20 (FIGS. 1, 7) for suitably inserting or engaging the wire or wires 11 and the filaments 12 of the brush devices 10 into either of the interdental spaces a or b or c between the teeth 80 of the user and for moving or actuating the filaments 12 to clean the interdental spaces between the teeth of the users. The brush device 10 of the motorized interdental toothbrush 1 in accordance with the present invention further includes a wire segment 14 selectively, but not necessarily formed or extended or provided on the second or front or free end portion 15 of each of the wires 11 and having no filaments formed or provided thereon.

A gage 30, 31, 32, 33, 34 is further provided and disposed or attached to the front portion 15 of each of the wires 11 or of the wire segment 14 of each of the wires 11 of the brush devices 10 and arranged for allowing the wire segment 14 to be formed and provided or located between the gages 30-34 and the filaments 12. The gages 30-34 are preferably made of soft or rubber or plastic or resilient or other synthetic materials and includes a rounded or spatial or three dimensional or spherical structure for safely engaging with the user's gum and for safely inserting or guiding the wire or wires 11 and the filaments 12 of the brush devices 10 to engage into the interdental spaces a or b or c between the teeth 80 and thus for preventing the gum of the user from being hurt or injured by the wire or wires 11.

The gages 30-34 each include a size or outer diameter or slightly smaller than or corresponding to that of the respective filaments 12 for limiting or guiding the brush devices 10 to be inserted or engaged into the predetermined or suitable interdental spaces a or b or c between the teeth 80 and for preventing the brush devices 10 of greater sizes or diameters from being inserted or engaged into the interdental spaces a or b or c having relatively smaller sizes or widths. For example, the gages 30-31 (FIGS. 2, 3) may be inserted or engaged into all of the interdental spaces a, b, c, but the other greater brush devices 10 (FIGS. 4-6) may be prevented from being inserted or engaged into the relatively smaller interdental space b by the gages 32-34.

Figure 4:
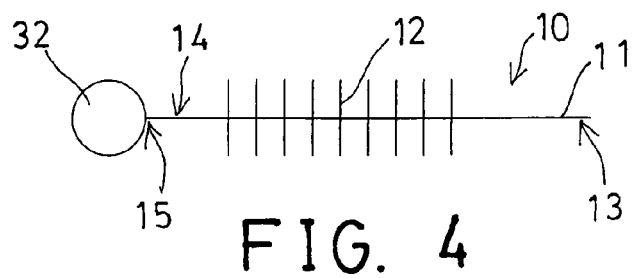
FIG. 4 is a partial plan schematic view similar to FIGS. 2 and 3, illustrating the further interdental toothbrush.

Similarly, the greater brush devices 10 as shown in FIGS. 4-6 may be limited and guided to be inserted or engaged into the relatively greater interdental spaces a, c, except the relatively smaller interdental space b by the gages 32-34, and the greatest gage 34 may limit and guide the brush devices 10 as shown in FIG. 6 to engage into the greatest interdental spaces c only but not the relatively smaller interdental spaces a and b, or the greatest gage 34 may limit and prevent the brush devices 10 as shown in FIG. 6 from being inserted or engaged into the relatively smaller interdental spaces a and b. The gages 32-34 have been disclosed and claimed in a co-pending U.S. patent application Ser. No. 11/715,061, filed 6 Mar. 2007.

Figure 7:
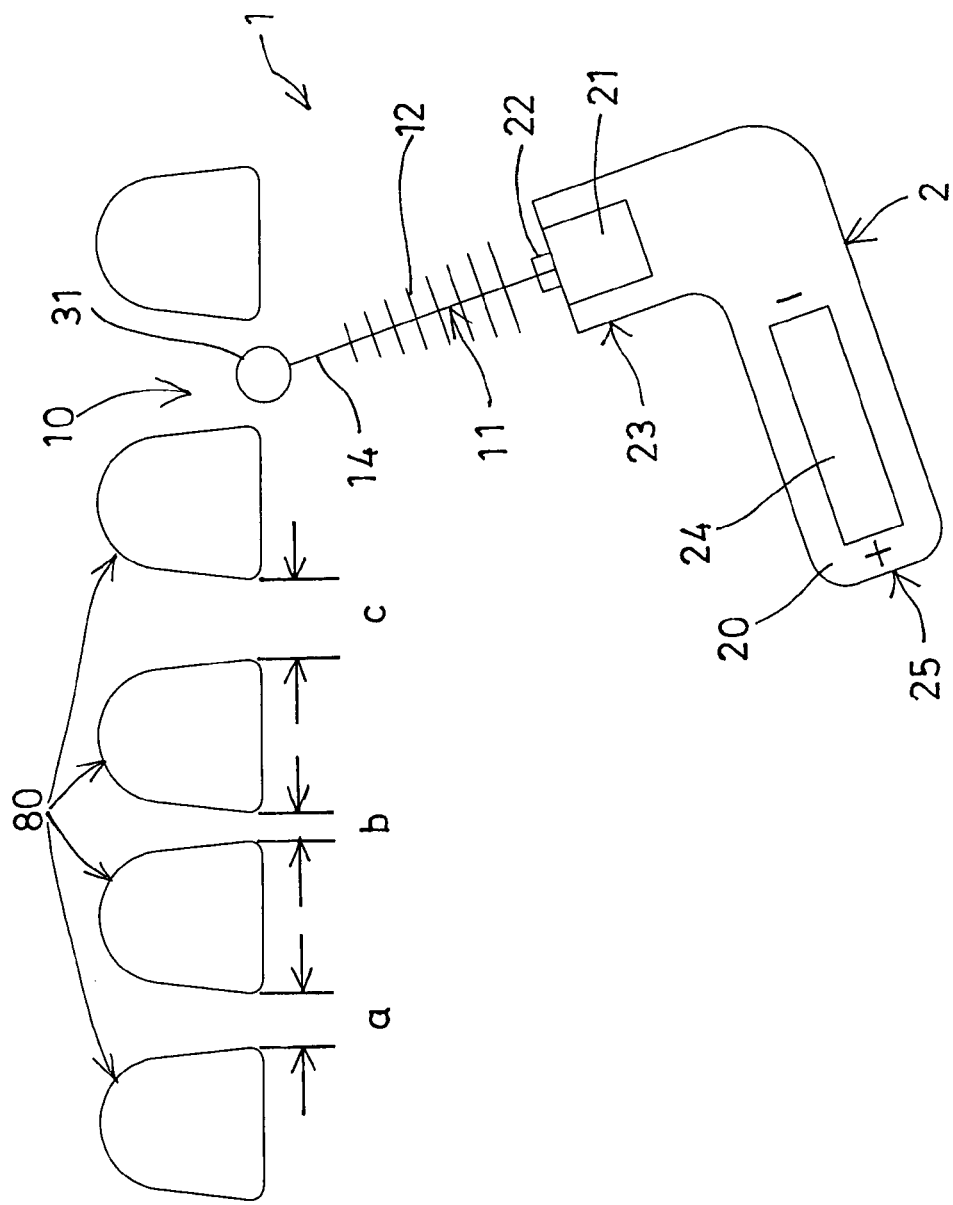
FIG. 7 is a partial perspective view illustrating the operation of the motorized interdental toothbrush.

As shown in FIGS. 1 and 7, the power or motor driving or rotating device 2 includes a motor 21 disposed or inserted or engaged into the handle 20, such as disposed in the front portion 23 of the handle 20 and having a spindle 22 directly coupled to the wires 11 or indirectly coupled to the wires 11 of the brush devices 10 with a reduction gearing (not shown) for rotating or driving the wire or wires 11 and the filaments 12 of the brush devices 10 to suitably clean the predetermined or suitable or selected interdental spaces a, b, c between the teeth. One or more batteries 24 may further be provided and disposed or inserted or engaged into the rear portion 25 of the handle 20 and coupled to the motor 21 for energizing or operating or actuating the motor 21 to rotate or drive or operate the wire or wires 11 and the filaments 12 of the brush devices 10.

The brush devices 10 may thus be limited and guided to be inserted or engaged into only the predetermined or suitable or relatively greater interdental spaces between the teeth, and may prevent the brush devices 10 of greater sizes or diameters from being inserted or engaged into the interdental spaces having relatively smaller sizes or widths, and thus may prevent the gum of the user from being hurt or injured by the filaments 12 of the brush devices 10 having relatively greater sizes or diameters. In addition, the rounded or spatial or three dimensional or spherical gages 30-34 may also prevent the gum of the user from being hurt or injured by the wire or wires 11.

Accordingly, the motorized interdental toothbrush in accordance with the present invention includes a motor driving means or device coupled to the interdental toothbrush for rotating or driving the interdental toothbrush and for allowing the interdental spaces to be suitably cleaned by the motorized interdental toothbrushes, and includes a gage for guiding the interdental toothbrush to be inserted or engaged into the predetermined or suitable interdental spaces between the teeth and for preventing the interdental toothbrushes of greater sizes or diameters from being inserted or engaged into the interdental spaces having relatively smaller sizes or widths.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A motorized interdental toothbrush comprising:

a brush device including at least one wire, and filaments disposed on said at least one wire for inserting and engaging into an interdental space between teeth of a user, and including a gage disposed on a free end portion of said at least one wire and having an outer diameter substantially equal to that of said filaments for limiting said at least one wire and said filaments to engage into a predetermined interdental space between the teeth of the user and for preventing said filaments from being inserted and engaged into an interdental space having a relatively smaller width and for preventing the user's gum from being hurt or injured by said filaments, and means for rotating said brush device to clean the interdental space between the teeth of the user.

2. The motorized interdental toothbrush as claimed in claim 1, wherein said rotating means includes a handle, and a motor disposed in said handle and coupled to said at least one wire of said brush device for rotating and driving said at least one wire and said filaments of said brush device to clean the interdental space.

3. The motorized interdental toothbrush as claimed in claim 2, wherein said motor includes a spindle coupled to said at least one wire of said brush device.

4. The motorized interdental toothbrush as claimed in claim 2, wherein said rotating means includes a battery disposed in said handle and coupled to said motor for energizing said motor to rotate said brush device.

5. The motorized interdental toothbrush as claimed in claim 1, wherein said at least one wire includes a wire segment provided thereon and located between said gage and said filaments.

6. The motorized interdental toothbrush as claimed in claim 1, wherein said gage includes an outer diameter equal to that of said filaments.

7. The motorized interdental toothbrush as claimed in claim 1, wherein said gage includes an outer diameter smaller than that of said filaments.

8. The motorized interdental toothbrush as claimed in claim 1, wherein said gage is made of soft materials for preventing the user's gum from being hurt and injured by said at least one wire.

9. The motorized interdental toothbrush as claimed in claim 1, wherein said gage includes a rounded structure.

10. The motorized interdental toothbrush as claimed in claim 1, wherein said gage includes a spherical structure.

* * * * *